United States Patent [19]

Matsuzaki et al.

[11] Patent Number: 5,061,498

[45] Date of Patent: Oct. 29, 1991

[54] METHOD FOR REFORMING FATS AND OILS WITH ENZYMES

[75] Inventors: Narihide Matsuzaki; Jun Kurashige, both of Kawasaki; Tamio Mase, Ichinomiya; Shotaro Yamaguchi, Aichi, all of Japan

[73] Assignee: The Japanese Research & Development Association for Bioreactor System in Food Industry, Tokyo, Japan

[21] Appl. No.: 365,809

[22] Filed: Jun. 14, 1989

[30] Foreign Application Priority Data

Jun. 14, 1988 [JP] Japan ............................. 63-144690

[51] Int. Cl.$^5$ ..................... A23D 7/00; C12P 7/62
[52] U.S. Cl. ................................. 426/33; 426/601; 435/134; 435/135
[58] Field of Search ................. 426/33, 601, 602–604; 435/134, 135, 176, 198

[56] References Cited

U.S. PATENT DOCUMENTS 4,275,081  6/1981  Coleman et al. .................. 426/33
4,719,178  1/1988  Macrae et al. .................... 426/33

FOREIGN PATENT DOCUMENTS 3302929 12/1988 Japan ................................. 426/33

Primary Examiner—Marianne Cintins
Attorney, Agent, or Firm—Oblon, Spivak, McClelland, Maier & Neustadt

[57] ABSTRACT

The present invention relates to a method for reforming fats and oils which comprises treating the fats and oils containing partial glycerides with two or more kinds of lipases which are different in a fatty acid specificity and/or a position specificity in the presence of a small amount of water to obtain fats and oils containing partial glycerides in a low content in a high yield. According to the invention, a reaction rate and a yield are improved.

17 Claims, No Drawings

METHOD FOR REFORMING FATS AND OILS WITH ENZYMES

BACKGROUND OF THE INVENTION

1. Field of the Invention

This invention relates to a method for reforming fats and oils with enzymes, and more specifically relates to a method for reforming fats and oils which comprises treating the fats and oils with two or more kinds of lipases to convert diglycerides and/or monoglycerides (hereinafter these glycerides are collectively referred to as partial glycerides) included in the fats and oils to triglycerides (hereinafter abbreviated as TG).

In other words, the invention relates to a method for reforming fats and oils which comprises converting the partial glycerides contained as impurities in the fats and oils to obtain fats and oils having a high TG content, namely fats and oils having a low partial glyceride content in a high yield.

Enhancement of the TG content in fats and oils leads to solid fats having a high melting point and good quality, and thus contributes to the industry of food such as chocolate.

2. Description of the Prior Art

Fats and oils generally contain esters of fatty acid(s) and glycerol, i.e. TG as a main component, and contain as components other than TG small amounts of partial glycerides, free fatty acids and unsaponifiable matters.

Partial glycerides included in fats and oils include, for example, those synthesized in the living bodies of animals and plants and microorganisms, those produced by partial hydrolysis of TG by the action of lipase contained therein or by a non-enzymatic action during the preservation of the fats and oils, or those produced as by products in the steps of processing of fats and oils such as ester interchange or synthesis of fats and oils from fatty acid(s) and glycerol. In natural fats and oils, palm oil recovered from the sarcocarp of *Elaeis guineensis* and olive oil recovered from the fruit of *Olea europaea* have a high water content and are susceptible to hydrolysis with enzymes during the recovering steps and preservation of the fats and oils, and rice bran which is a raw material of rice oil has a strong lipase activity. For the above or other reasons, fats and oils prepared therefrom generally have a high partial glyceride content.

As methods of removing impurities in fats and oils, there have been carried out alkali purification for the purpose of the removal of fatty acids, vacuum steam distillation for the purpose of the removal of odor components and other volatile components and fatty acids, and degumming for the purpose of the removal of gummy matters, carbohydrates, proteins, etc. Removal of these impurities is relatively easy. On the other hand, mutual separation of TG, diglyceride (hereinafter abbreviated as DG) and monoglyceride (hereinafter abbreviated as MG) has been carried out only by means for their analysis, namely by methods such as column chromatography and thin layer chromatography using silica gel as well as gel permeation chromatography utilizing molecular sieve effect. Further, for the purpose of the removal of fatty acids and the fractionation of TGs contained in fats and oils, there have been carried out fractional crystallization utilizing the difference in melting point of TGs, liquid-liquid extraction utilizing the difference in solubility in solvents, fractional distillation utilizing the difference in boiling points and molecular distillation. By these methods, removal of MG was more or less effected but removal of DG was difficult.

Recently, as a method of removing partial glycerides using an enzyme, there has been reported a method of specifically hydrolyzing and removing partial glycerides in fats and oils utilizing a partial glyceride lipase which has no or almost no reactivity with TG (Japanese Patent Unexamined Published Application No. 62-287). On the other hand, there has been reported a method of obtaining fats and oils having a high TG content by ester synthesizing TGs from partial glycerides and fatty acids with triglyceride lipase in the presence of water of 100 ppm or less (J. Am. Oil Chem. Soc. 64(9), 1252(1987).

The removal of partial glycerides from fats and oils by chromatography might be possible in a laboratory scale but could scarcely be adopted in an industrial scale. Further, by the means for the separation of TG components in fats and oils, it was impossible to separate DG and TG from each other since they form an eutectic mixture. Thus, it has hitherto been desired to industrially remove partial glycerides from fats and oils, but there has been no method suitable for the purpose.

Existence of partial glycerides has various undersirable influences on fats and oils. First, partial glycerides have an action of inhibiting the formation of crystalline nuclei of TG. For example, the existence of MG of about 2% or more in palm oil inhibits the growth of crystalline nuclei of TG and the existence of DG of about 13% in the same oil awfully elongates the life time of $\alpha$-type crystals. Further, it is generally considered that the existence of DG in fats and oils or fat and oil products inhibits the transformation of TG crystals from $\beta'$-type to $\beta$-type [Olea giniaux, 29, 421(1974); Oil Palm News, 22, 10–18(1977); J. Sci. Food Agric. 32, 1197(1981); and Fette Seifen An strichm, 85, 64(1983)].

Fruther, DG forms with TG an eutectic mixture which in turn not only makes the separation of these components difficult but also reduces the solid fat index of the fats and oils. As a result, apparent content of high melting TG having relation to crystal becomes lower than the actual content, yield of the solid components is lowered and at the same time a part of the solid components remains in the liquid components, and thus the fractionation of TG becomes incomplete. Further, partial glycerides themselves have an emulsifying action, and thus in the fractionation of TG crystals using a polar organic solvent, lower the separation efficiency.

In fat and oil products such as cacao substitute fats wherein a sharp melting point is required, partial glycerides make the melting point of the products unclear and broad.

For solving this problem, there have been proposed two methods wherein an enzyme is used. One is a method wherein DG is removed with hydrolysis using a partial glyceride lipase and which has an advantage of requiring no complicated reactors. But according to this method, it is impossible to avoid the lowering of yield of purified fats and oils because of hydrolysis.

The other is one wherein partial glycerides and fatty acids are treated with a lipase in the presence of water in a small amount to ester-synthesize TG. This method is excellent in that it is possible not only to reduce fatty acids and partial glycerides as impurities in fats and oils but also to increase the yield of TG. However, in order to put this method in practical use, it is necessary to enhance the ability of an enzyme to be used and to develop a new reactor.

SUMMARY OF THE INVENTION

An object of the invention is to provide a method for reforming fats and oils with enzymes wherein the performance of the enzymes are enhanced and an enzymatic reaction having a high reaction rate and a high yield is established.

The present inventors have vigorously studied for solving the above problems, have found that a high reaction rate and a high yield which have never been accomplished by single use of each enzyme, can be attained by using plural enzymes having different properties to make the best use of merits of each enzyme or to mutually make up for the drawbacks. and have accomplished the present invention.

That is, the invention relates to a method for reforming fats and oils which comprises treating the fats and oils containing partial glycerides with a lipase in the presence of a small amount of water to obtain fats and oils containing partial glycerides in a low content in a high yield, wherein the starting fats and oils are treated with two or more kinds of lipases. The use of plural kinds of lipases increases a reaction rate and a yield and thus shortens a reaction time.

Lipases are different in not only general properties such as reaction temperature dependency, reaction pH dependency, temperature and pH stability but also in fatty acid specificity, position specificity, etc. Fatty acid specificity means the differences in reactivities between substrates which are free fatty acids or fatty acid esters in reactions catalyzed by lipases, i.e. ester hydrolysis, ester synthesis or ester interchange reactions. Position specificity means the differences in reactivities between the hydroxyl groups at the 1-, 2- and 3-positions of the glycerol.

When lipases are utilized for the purpose of ester synthesis, ester interchange, flavour formation, etc. in the field of the fats and oils industry, they are properly selected and used for the purposes taking the differences into account.

In the reaction of the invention as well, lipases are selected and used taking the characteristics thereof. For example, in the previous report [J. Am. Oil Chem. Soc. 64(9), 1252(1987)], lipase P derived from Pseudomonas is selected as an enzyme having the highest synthetic activity, which is low in a position specificity, in other words which easily acts on any of the three hydroxyl groups of glycerol.

This means that since partial glycerides present in fats and oils, particulary DGs which composes the greater part thereof exist as a mixture of two kinds of position isomers, i.e. 1,3-diglyceride and 1,2(or 2,3)-diglyceride, it is more preferable to use a lipase acting on the hydroxyl group at the 2-position of glycerol as well as the hydroxyl groups at the 1- and 3-positions thereof than a lipase having a high specificity to the 1- and 3-positions.

However, as indicated in Test example 2 described later, the amount of enzyme to be used is severely restricted in view of cost and sufficient reaction rate and reaction completion extent have never been obtained even lipase P having the highest activity is used.

In the course of detail investigation of the synthetic reaction using various lipases related to the invention, the present inventors have found that lipase P has an extremely low reactivity with oleic acid among free fatty acids present in fats and oils compared to that with palmitic acid also present therein, whereas a certain kind of lipase, for example lipase F (made by Amano Pharmaceutical Co., Ltd. Japan) produced by a strain of the genus Rhizopus and having 1,3-position specificity sufficiently acts on oleic acid as well as palmitic acid.

This fact, namely the differences in fatty acid specificity of various kinds of lipases is explained in detail in the following Test example 1.

Further, as indicated in the following Test example 2 there has been a limit in reaction rate and reaction completion extent in case of single use of each enzyme. This would be because that lipase P has an advantage of low position specificity but has only a poor reactivity with oleic acid and lipase F has an advantage of having no fatty acid specificity but has a high 1,3-specificity and thus does not easily act on the hydroxyl group at the 2-position.

Thus, the present inventors have come up with an idea to make the both enzymes act on fats and oils and accomplished, by their synergistic effect, a high reaction rate and a high yield, and have completed the invention.

Lipases used in the invention includes those originated from microorganisms, animals and plants so long as they exhibit activities in the reaction system of TG synthesis. There are exemplified as those having a low position specificity, lipases derived from the genera Pseudomonas, Candida and Penicillium and as those having a high 1,3-specificity, lipases derived from the genera Aspergillus, Rhizopus, Mucor and Alcaligenes and lipases derived from the pancreas of animals and so on.

According to the classification based on the differences in fatty acid specificity, there are exemplified as those easily acting on short chained fatty acids, lipases derived from the genus Penicillium, etc., as those easily acting on middle chained fatty acids, lipases derived from the genus Rhizopus, etc., as those acting on all fatty acids including long chained fatty acids, lipases derived from *Candida Cylindracea*, etc. and as those highly acting on unsaturated fatty acids, lipases derived from *Geotricum candidum*, etc.

Selection of lipases may suitably be carried out in accordance with the kind of free fatty acids in fats and oils to be treated. Further, in the invention wherein plural lipases are used, any combination and amount ratio of these lipases can be used so long as the effect of the invention is attained.

Fats and oils usable in the invention include those containing a large amount of partial glycerides, i.e. MG and DG, for example, palm oil, rice oil, corn oil and olive oil. Of course there arises no problem if fats and oils other than the above are used, for example, liquid fats such as rapeseed oil, safflower oil and soybean oil and solid fats such as lard, tallow and beef kennen fat, and the above fats and oils which have been processed such as those subjected to subsequent fractionation, hydrogenation, ester interchange or other treatment.

Further, it is possible, if necessary, to add to the above fats and oils, fatty acids alone or in combination. Although there is no particular limitation about the amount to be added, addition of too much fatty acid only brings about the difficulty of purification of the fats and oils after the enzymatic reaction and lowers the yield. Thus, it is usually preferred to add fatty acids so that the ratio of the amount of the fatty acids to that of DG contained in the raw fats and oils is 0.5 to 10. Further, there is also no particular limitation about the kind of fatty acids to be added, and there may be added any of saturated fatty acids such as palmitic acid (hereinafter abbreviated as PA) and stearic acid and unsaturated fatty acids such as oleic acid (hereinafter abbreviated as OA) and linolic acid.

In the process of the present invention, lipases are used in a reaction system wherein water is removed as completely as possible in order to make the lipases act under an ester synthesis condition. Since the activity of the enzymes is not sufficiently displayed under the condition of such a low water content, it is usually preferred to use the enzymes in the form immobilized on an immobilizing carrier. Immobilizing carriers usable therefor include Celite, clay, cellulose and its derivatives, chitosan and its derivatives, adsorption type carriers such as ion exchange resins, photohardenable resins, inclusion type carriers such as sodium alginate.

Further, in order to enhance the activity of the enzymes under the condition in the invention, it is preferred to make a surfactant such as a sucrose fatty acid ester, lecitin, a sorbitan fatty acid ester or a polyglycerin fatty acid ester coexist at the preparation of the immobilized enzyme preparation. The amount of the surfactant to be added is preferably 10 to 500 weight % of the enzymes.

Although the amount of the immobilized enzymes to be added to fats and oils is not particularly limited, it is usually suitable to add them in an amount of 20 to 30% of the raw fats and oils.

Although the reaction temperature can be selected suitably in accordance with the optimum temperature of immobilized lipase enzymes and the melting point of fats and oils to be used, a temperature of 20° to 80° C. is usually preferred.

As for water content, lipases catalyze the reversible reaction between partial glycerides and TG. When there is much water, lipases catalyze hydrolysis, whereas they catalyze a synthetic reaction when there is only a small amount of water. Therefore, a condition for removing water as completely as possible is necessary in the invention. Although the water concentration is varied depending on the concentration of diglycerides and fatty acids in fats and oils to be used in the reaction, it is usually preferred to adjust water content of the reaction system to 1500 ppm or less, particularly 10 to 200 ppm.

Removal of water can be carried out by distillation under reduced pressure, use of a dehydrating agent such as molecular sieves, use of an inert dry gas such as nitrogen gas, etc.

The process of the present invention can be carried out in any of batch reaction method, continuous reaction method using a bioreactor such as a column method or fluid bed method, etc.

Although the present invention can sufficiently be achieved even in the absence of a solvent, an organic solvent may be added if necessary. Any of organic solvents which do not inhibit the activity of lipases and can dissolve fats and oils can be used, and examples of such solvents are n-hexane, octane, petroleum ether, diethyl ether, acetone, ethyl acetate, etc.

Further, the processes of treating fats and oils with plural lipases in the invention can, for example, be carried out either by a procedure wherein plural lipases are simultaneously immobilized at the preparation of the immobilized enzymes, by a procedure wherein plural immobilized enzyme preparations obtained by separate immobilization are mixed and used at the time of reaction, or in case where a reactor is used, by a procedure wherein each immobilized enzyme preparation is packed into respective reaction layers or towers connected in series to which the raw fats and oils are supplied.

The present invention is further described below by test examples and working examples. "%" in these examples is by weight unless otherwise indicated.

TEST EXAMPLE 1

Lipase P (made and sold by Amano Pharmaceutical Co., Ltd.) derived from a strain of the genus Pseudomonas and lipase F (made and sold by Amano Pharmaceutical Co., Ltd.) derived from a strain of the genus Rhizopus were used. In case of lipase P, 20 mg of the enzyme powder and 10 mg of sugar ester 0-1570 (made by Mitsubishi Kasei Co., Ltd.), and in case of lipase F, 40 mg of the enzyme powder and 20 mg of the suger ester were dissolved in 2 ml of water, respectively. These aqueous solutions were, respectively, uniformly spread over 2 g of Celite No. 535 to immobilize the enzyme on the carrier, and the resulting Celites were dried under the reduced pressure of 5 mmHg to remove unnecessary water. 2 g of the thus obtained immobilized enzyme preparations were added, respectively, to 20 g of purified palm olein oils to which PA or OA as a fatty acid (hereinafter abbreviated as FFA) was added, and the reaction was carried out with shaking at 60° C. 12 g of Molecular Sieves 3A (tradename, made by Wako Junyaku Co., Ltd.) was added thereto as a dehydrating agent at the same time. After the reaction, fats and oils were separated, respectively, from the immobilized enzyme preparation and the molecular sieves, and analyzed for its composition by gas chromatography. The results are shown in Table-1.

TABLE 1

| Oils treated | Enzyme | Time (hr) | FFA (%) PA | FFA (%) OA | MG (%) | DG (%) | TG (%) |
|---|---|---|---|---|---|---|---|
| Palmitic acid -added purified palm olein | Before reaction | — | 3.96 | 0.26 | 1.10 | 5.09 | 90.59 |
| | Lipase P | 4 | 3.58 | 0.34 | 0 | 3.45 | 92.63 |
| | | 24 | 2.26 | 0.32 | 0 | 2.00 | 95.42 |
| | Lipase F | 4 | 3.43 | 0.47 | 0 | 2.35 | 93.75 |
| | | 24 | 1.84 | 0.35 | 0 | 1.90 | 95.91 |
| Oleic acid -added purified palm olein | Before reaction | — | 0.24 | 4.49 | 0.10 | 5.02 | 90.15 |
| | Lipase P | 4 | 0.30 | 3.69 | 0 | 4.77 | 91.24 |
| | | 24 | 0.49 | 3.86 | 0 | 4.70 | 90.95 |
| | Lipase F | 4 | 0.05 | 2.92 | 0 | 3.42 | 93.61 |
| | | 24 | 0.47 | 2.32 | 0 | 2.44 | 94.77 |

It is seen from Table-1 that the reactivity of lipase P with oleic acid is extremely low compared to that with palmitic acid, whereas lipase F has an equal reactivity with oleic acid and palmitic acid.

TEST EXAMPLE 2

Preparation of immobilized enzymes, reaction and analysis were carried out in the same manner as in Test example 1 except that each 40 mg of the two enzymes lipase P and lipase F and 20 mg of a sugar ester (0-1570) were used and crude palm olein was used as an oil to be treated. The results are shown in Table-2.

TABLE 2

| Oil treated | Enzyme | Time (hr) | FFA (%) PA | FFA (%) OA | MG (%) | DG (%) | TG (%) |
|---|---|---|---|---|---|---|---|
| Crude palm olein | Before reaction | — | 2.10 | 2.72 | 0.20 | 7.79 | 87.19 |
| | Lipase P | 4 | 1.47 | 2.07 | 0 | 3.83 | 92.63 |
| | | 24 | 1.15 | 2.10 | 0 | 3.77 | 92.98 |

TABLE 2-continued

| Oil treated | Enzyme | Time (hr) | FFA (%) PA | FFA (%) OA | MG (%) | DG (%) | TG (%) |
|---|---|---|---|---|---|---|---|
| | Lipase F | 4 | 1.48 | 1.88 | 0 | 4.17 | 92.47 |
| | | 24 | 1.00 | 1.26 | 0 | 4.58 | 93.16 |

It is seen from Table-2 that in case of both enzymes, after the TG content had reached about 92.5% in 4 hours, only a slight increase was observed, and the content was about 93% even at 24 hours.

EXAMPLE 1

Preparation of immobilized enzyme, reaction and analysis were carried out in the same manner as in Test example 1 except that 20 mg of lipase P, 20 mg of lipase F and 20 mg of sugar ester (0-1570) were simultaneously dissolved in 2 ml of water and crude palm olein was used as an oil to be treated. The results are shown in Table-3.

EXAMPLE 2

Preparation of immobilized enzyme, reaction and analysis were carried out in the same manner as in Test example 1 except that 13.3 mg of lipase P, 26.7 mg of lipase F and 20 mg of sugar ester (0-1570) were simultaneously dissolved in 2 ml of water and crude palm olein was used as an oil to be treated. The results are shown in Table-3.

EXAMPLE 3

Preparation of immobilized enzyme, reaction and analysis were carried out in the same manner as in Test example 1 except that 26.7 mg of lipase P, 13.3 mg of lipase F and 20 mg of sugar ester (0-1570) were simultaneously dissolved in 2 ml of water and crude palm olein was used as an oil to be treated. The results are shown in Table-3.

EXAMPLE 4

0.67 g of an immobilized enzyme prepared in the same manner as in Test example 1 using 40 mg of lipase P and 20 mg of sugar ester (0-1570), and 1.33 g of an immobilized enzyme prepared in the same manner as in Test example 1 using 40 mg of lipase F and 20 mg of sugar ester (0-1570) were mixed and then 20 g of crude palm olein was added thereto, and then reaction and analysis were carried out in the same manner as Test example 1. The result is shown in Table-3.

TABLE 3

| Oils treated | Reaction | Time (hr) | FFA (%) PA | FFA (%) OA | MG (%) | DG (%) | TG (%) |
|---|---|---|---|---|---|---|---|
| Crude palm olein | Before reaction | — | 2.10 | 2.72 | 0.20 | 7.79 | 87.19 |
| | Example 1 | 4 | 1.06 | 1.27 | 0 | 1.89 | 95.78 |
| | | 24 | 0.62 | 0.78 | 0 | 1.39 | 97.21 |
| | Example 2 | 4 | 1.09 | 0.28 | 0 | 3.27 | 94.36 |
| | | 24 | 0.57 | 1.66 | 0 | 1.32 | 97.45 |
| | Example 3 | 4 | 1.22 | 1.65 | 0 | 2.54 | 94.59 |
| | | 24 | 0.59 | 0.90 | 0 | 1.70 | 96.81 |
| | Example 4 | 24 | 0.91 | 1.27 | 0 | 3.53 | 94.29 |

It is apparent from the comparison of the results of Table-3 with those of Table-2 that when lipase P and lipase F were simultaneously used, remarkable increases in reaction rates and yields were observed compared to the case where only one of the enzymes was used. As shown in Table-2, TG contents at 4 and 24 hours in case of use of lipase P alone were 92.63% and 92.98% respectively, and TG contents at 4 and 24 hours in case of use of lipase F alone were 92.47% and 93.16% respectively. In contrast, as shown in Table-3, TG content in case of simultaneous use of both enzymes was 94.36% to 95.78% at 4 hours. This indicates that the simultaneous use brought about remarkable increases of reaction rates. Increase was also apparently observed in a yield at 24 hours.

EXAMPLE 5

100 g of an immobilized enzyme preparation prepared in the same manner as in Test example 1 using 1 g of lipase P, 1 g of lipase F, 1 g of sugar ester (0-1570) and 100 g of Celite No. 535 was added to 1000 g of crude palm olein having the composition consisting of 87.2% TG, 4.8% fatty acids, 7.8% DG and 0.2% MG, and the mixture was subjected to a reaction under the reduced pressure of 10 mmHg at 60° C. for 24 hours with stirring. After completion of the reaction, the immobilized enzyme preparation was removed by filtration and the resulting reaction oil was subjected to usual steam distillation to remove unreacted fatty acids, whereby 980 g (yield 98.0%) of purified oil was obtained. The results shown in Table-4 reveals that the reaction with both enzymes is shorter in reaction time and higher in yield than the reaction with one of the enzymes.

TABLE 4

| | Weight (g) | FA (%) | MG (%) | DG (%) | TG (%) |
|---|---|---|---|---|---|
| Raw oil | 1000 | 4.8 | 0.2 | 7.8 | 87.2 |
| Purified oil | 980 | 0 | 0 | 1.4 | 98.6 |

As is understood from the foregoing general description and specific examples, according to the present invention, a reformed oil having a low partial glyceride content is obtained in a high yield and in a shorter time by treating fats and oils with two or more kinds of lipases to convert the partial glycerides to TG.

Further, the obtained reformed oil has low MG and DG contents, which means that purification is conducted in a high yield and low cost.

What is claimed is:

1. A method for reforming fats and oils, which comprises:
   treating the fats and oils with at least two lipases which are different in fatty acid specificity and/or position specificity, with the lipase having different fatty acid specificity being selected from the group consisting of lipases acting on short chained fatty acids, lipases acting on middle chained fatty acids, lipases acting on all fatty acids and lipases acting on unsaturated fatty acids, and said lipase having different position specificity being selected from the group consisting of lipases having no position specificity and lipases having 1,3-position specificity, thereby converting the partial glycerides within the fats and oils to triglycerides.

2. The method of claim 1 wherein a lipase having no fatty acid specificity but a 1,3-position specificity and a lipase having no position specificity but a fatty acid specificity are used together.

3. The method claim 1 wherein both lipase P and lipase F are used.

4. The method of claim 1 wherein the fats and oils are liquid fats and oils or solid fats and oils, or processed fats and oils.

5. The method of claim 4 wherein the fats and oils are those processed by fractionation, hydrogenation or interesterification.

6. The method of claim 1 wherein the fats and oils are selected from the group consisting of palm oil, rice oil, corn oil, olive oil, rapeseed oil, safflower oil, soybean oil, lard, tallow and beef kennen fat; processed fats and oils selected from the above group; and mixtures of the above.

7. The method of claim 1 wherein at least one fatty acid is added to the reaction system.

8. The method of claim 7 wherein the amount of the fatty acid to be added is 0.5 to 10 times the weight of diglycerides contained in the fats and oils.

9. The method of claim 1 wherein the water content of the reaction system is 1500 ppm or less.

10. The method of claim 1 wherein lipases are used in the form immobilized on an immobilizing carrier.

11. The method of claim 10 wherein a surfactant is made to coexist at the preparation of the immobilized lipase.

12. The method of claim 11 wherein the amount of the immobilized enzymes to be added to the fats and oils is 2 to 30% by weight based on the fats and oils.

13. The method of claim 1 wherein the reaction temperature is 20° to 80° C.

14. The method of claim 1 wherein the reaction is carried out in the absence of or in the presence of an organic solvent.

15. The method of claim 1 wherein an enzyme preparation obtained by simultaneously immobilizing two or more kinds of lipases on a carrier is used.

16. The method of claim 1 wherein two or more kinds of immobilized enzyme preparations obtained by separate immobilization are mixed and used.

17. The method of claim 1 wherein two or more kinds of immobilized enzyme preparations are packed into separate reaction layers or towers connected in series through which the fats and oils are passed.

* * * * *